(12) United States Patent
Fiere (10) Patent No.: US 10,905,631 B2
(45) Date of Patent: Feb. 2, 2021

(54) NEEDLELESS SYRINGE CONNECTOR CAP AND CONTAINER

(71) Applicant: Scholle IPN IP BV, SX Tilburg (NL)

(72) Inventor: Jeroen Pieter Fiere, VH 'S-Gravendeel (NL)

(73) Assignee: Scholle IPN IP BV, SX Tilburg (NL)

( * ) Notice: Subject to any disclaimer, the term of this patent is extended or adjusted under 35 U.S.C. 154(b) by 408 days.

(21) Appl. No.: 16/064,504

(22) PCT Filed: Dec. 21, 2016

(86) PCT No.: PCT/NL2016/050899
§ 371 (c)(1),
(2) Date: Jun. 21, 2018

(87) PCT Pub. No.: WO2017/111584
PCT Pub. Date: Jun. 29, 2017

(65) Prior Publication Data
US 2019/0000716 A1    Jan. 3, 2019

(30) Foreign Application Priority Data
Dec. 22, 2015   (NL) ..................... 2016005

(51) Int. Cl.
*A61J 1/20* (2006.01)
*A61M 39/26* (2006.01)
*A61M 39/04* (2006.01)
*A61J 1/14* (2006.01)
*B65D 51/00* (2006.01)
*A61M 39/02* (2006.01)
*A61M 39/20* (2006.01)
*A61M 39/00* (2006.01)

(52) U.S. Cl.
CPC .......... *A61J 1/2037* (2015.05); *A61J 1/1406* (2013.01); *A61J 1/1418* (2015.05); *A61J 1/1487* (2015.05); *A61J 1/2048* (2015.05); *A61J 1/2072* (2015.05); *A61M 39/04* (2013.01); *A61M 39/045* (2013.01); *A61M 39/26* (2013.01); *B65D 51/002* (2013.01); *A61M 39/20* (2013.01); *A61M 2039/0036* (2013.01); *A61M 2039/0072* (2013.01); *A61M 2039/0202* (2013.01); *A61M 2039/0205* (2013.01)

(58) Field of Classification Search
CPC .. A61J 1/2037; A61J 1/20; A61J 1/202; A61J 1/2024; A61J 1/2041; A61J 1/2044;
(Continued)

(56) References Cited

U.S. PATENT DOCUMENTS 9,095,500 B2 * 8/2015 Brandenburger .... B65D 51/002
2003/0018305 A1    1/2003 Tsai
(Continued)

FOREIGN PATENT DOCUMENTS

DE    102008060864 A1    6/2010
FR    2539300 A1    7/1984
(Continued)

*Primary Examiner* — Philip R Wiest
(74) *Attorney, Agent, or Firm* — The Watson IP Group, PLC; Jovan N. Jovanovic (57) ABSTRACT

A needleless syringe connector cap to be provided to a container having an aperture at its top, said cap comprising an elastically deformable plastic valve body. Said valve body comprises a first and second passage, each passage extending through the valve body. Both passages comprise a cross-slit valve in the extreme lower end of said passage, embodied as an aeration valve. The first passage is adapted to receive a first tapered syringe tip and the second passage is adapted to receive a second tapered syringe tip, wherein when fluid is withdrawn from a container to which the cap is provided through the first (second) passage using a first (second) tapered syringe tip to which said first (second) passage is adapted, the second (first) cross-slit valve opens in response to an under pressure in said container resulting from said withdrawal, so as to aerate said container.

20 Claims, 8 Drawing Sheets

(58) Field of Classification Search
CPC ...... A61J 1/2058; A61J 1/2068; A61J 1/2072; A61J 1/2075; A61J 1/1418; A61J 1/1487; A61J 1/1406; A61M 39/04; A61M 39/045; A61M 39/26; A61M 39/20; A61M 2039/0069; A61M 2039/0072; A61M 2039/0202; A61M 2039/0205
See application file for complete search history.

(56) References Cited

U.S. PATENT DOCUMENTS

| | | | |
|---|---|---|---|
| 2004/0112855 A1* | 6/2004 | Becker | B65D 51/002 215/247 |
| 2007/0027437 A1 | 2/2007 | Burg et al. | |
| 2009/0054865 A1* | 2/2009 | Brandenburger | B65D 51/002 604/415 |
| 2011/0245796 A1* | 10/2011 | Brandenburger | A61J 1/1418 604/414 |
| 2013/0037509 A1* | 2/2013 | Rahimy | A61J 1/1481 215/247 |
| 2017/0079880 A1* | 3/2017 | Guala | A61J 1/2082 |

FOREIGN PATENT DOCUMENTS

| | | |
|---|---|---|
| WO | 02064077 A1 | 8/2002 |
| WO | 03079956 A1 | 10/2003 |
| WO | 2005037362 A1 | 4/2005 |

* cited by examiner

NEEDLELESS SYRINGE CONNECTOR CAP AND CONTAINER

The present invention relates to the field of caps to be provided to containers, and more specifically relates to caps that, when provided to a container, allow a fluid to be withdrawn from the interior of said container by means of a needleless syringe connector provided in said cap.

Withdrawal from a container of a fluid, e.g. fluid food or fluid medication such as fluid animal food or fluid animal medication, is often performed using a needle that punctures a septum of a cap provided on the container. Said septum is made of a material, e.g. rubber, that allows to be punctured by a sharp and thin needle to withdraw fluid, but seals the fluid hermetically from the ambient prior to, and possibly also after, the puncture. The septum may be completely flat, or may only comprise a small mark indicating the optimal puncture point.

In some situations the administration of the fluid withdrawn from a container does not require a needle. This may for instance be when the fluid is provided to a feed tube or other type of catheter, or is administered orally to the patient, e.g. animal. Use of a needle may also be disadvantageous, as the use of a needle entails a risk of accidental sticking or injection. The use of a needleless syringe, that allows administering of a specific dose, but is provided with a blunt or needleless tip, may then be preferred.

When fluids are administered with a needleless syringe, it is most straightforward to withdraw a fluid from a container using only said needleless syringe. For said fluid withdrawal with a needleless syringe connector caps provided with a thin membrane, sometimes a membrane with one or more splits therethrough, are known, for instance from WO02064077. The needleless syringe tip can be forced through the thin membrane of said connector cap.

It is the object of the present invention to provide an improved connector cap to be provided to a container, said connector cap being suitable for withdrawal of fluids from a container using needleless syringes.

The inventive needleless syringe connector cap is to be provided to a container having an aperture at its top. Said cap comprises an elastically deformable plastic valve body that is to be provided in or above said aperture at the top of the container. Said valve body has a top surface and a bottom surface, wherein said valve body comprises a first passage and a second passage. Each passage extends through the valve body from the top surface to the bottom surface thereof.

In an embodiment the container is a bottle, e.g. a plastic bottle.

The first passage comprises a first cross-slit valve in the extreme lower end of said passage, wherein said first cross-slit valve is embodied as an aeration valve. The second passage comprises a second cross-slit valve in the extreme lower end of said passage, wherein said second cross-slit valve is embodied as an aeration valve.

The first passage is adapted to receive a first tapered syringe tip having a first diameter, e.g. a first Luer slip syringe tip or a first catheter syringe tip, in that said first tip is insertable into the first passage from the top surface of the valve body and in that the first passage seals around said first tip when said tip has been inserted into the first passage.

The second passage is adapted to receive a second tapered syringe tip having a second diameter, e.g. a second Luer slip syringe tip or a second catheter syringe tip, in that said second tip is insertable into the second passage from the top surface of the valve body and in that the second passage seals around said second tip when said tip has been inserted into the second passage.

When fluid is withdrawn from a container to which the inventive cap is provided through the first passage using a first tapered syringe tip to which said first passage is adapted, the second cross-slit valve opens in response to an underpressure in said container resulting from said withdrawal, so as to aerate said container. When fluid is withdrawn from a container to which the cap is provided through the second passage using a second tapered syringe tip to which said second passage is adapted, the first cross-slit valve opens in response to an underpressure in said container resulting from said withdrawal, so as to aerate said container.

As used herein to describe the cap and container the terms 'top', 'bottom' and 'downward', as well as similar terms describing an vertical orientation, refer to a storage orientation in which the inventive needless syringe connector cap is provided on a container and wherein a surface of said container is in contact with a substrate, wherein said surface in contact with a substrate that is at the opposite side of the container compared to the cap. When withdrawing fluid from said container, the container with cap is likely tilted with respect to said storage orientation and possibly even tilted upside down with respect thereto to facilitate said fluid withdrawal.

The inventive cap is to be provided to a container having an aperture at its top, and allows withdrawal of fluid from the interior of said container through a first and a second passage of said container. During withdrawal the cap and container will be tilted, possibly tilted upside down. Leakage of fluid from the container should in this orientation of the cap and container be avoided, as such leakage is messy and lead to loss of sometimes valuable fluid. During withdrawal fluid leakage may occur between the syringe tip and cap. In order to avoid such leakage, the first and second passage of the inventive cap are adapted to receive a respective first and second tapered syringe tip with which a fluid is to be withdrawn from a container. The first passage is amongst others adapted in that when the first tip extends through the first passage, said first passage seals around said first tapered syringe tip, thereby avoiding leakage between syringe tip and cap. Similarly, the second passage is amongst others adapted in that when the second tip extends through the second passage, said second passage seals around said second tapered syringe tip, thereby avoiding leakage between syringe tip and cap.

Naturally, leakage of fluid through said cap should be avoided at all times, thus also in the absence of fluid withdrawal. Therefore, the passages of the inventive cap are sealable. More specifically, each of said passages is provided with a cross-slit valve in the extreme lower end thereof, wherein each cross-slit valve allows to seal its passage.

The withdrawal of fluid as described above is accompanied by an underpressure in the container. Said underpressure should be removed, as it may hinder or render impossible the withdrawal of fluid from the container. Therefore, the cross-slit valves of the inventive cap are embodied as aeration valves that open in the event of an underpressure, so that ambient air can enter the container. More specifically, when fluid is withdrawn using the first tapered syringe tip that is inserted into the first passage, the second cross-slit valve opens in response to an underpressure in said container resulting from said withdrawal, so as to aerate said container. When fluid is withdrawn using the second tapered syringe tip that is inserted into the second cross-slit valve of the second passage, the first cross-slit valve opens in response to an underpressure in said container resulting from said withdrawal, so as to aerate said container.

The cross-slit valve thus combines the functions of allowing for fluid withdrawal using a needleless syringe and allowing for aeration. Altogether, said needleless syringe connector cap allows effective fluid withdrawal using selected tapered fitting syringe tips, whereby said cross-slit valves aerate to facilitate said withdrawal and seal to prevent leakage, and through the provision of passages that seal around said tapered syringe tips during withdrawal to avoid leakage.

In an embodiment the first and second passages have a different diameter, adapted to receive different diameter syringe tips.

In another embodiment the first and second passages have the same diameter, adapted to receive syringe tips with equal diameters.

The cap may thus comprise two passages that are each adapted to a Luer taper syringe tip. Said Luer taper syringe tips may have the same or a different diameter.

Similarly, the cap may comprise two passages that are each adapted to a catheter syringe tip. Said catheter syringe tips may have the same or a different diameter.

Similarly, the cap may comprise two passages that are each adapted to both a Luer taper syringe tip and a catheter syringe tip.

Preferably the first and/or second passage adapted to a Luer slip syringe tip is adapted to a Luer slip syringe tip with a diameter between 2 and 6 mm, e.g. 4 mm.

Preferably the first and/or second passage is adapted to a catheter syringe tip is adapted to a catheter syringe tip with a diameter between 4 and 8 mm, e.g. 6 mm. Preferably the first tapered syringe tip is a first Luer slip syringe tip and said first passage is further adapted to receive said first Luer slip tip in that a top section of said first Luer slip tip can be forced through the first cross-slit valve and in that the first passage seals around said first Luer slip tip when said top section of said first Luer slip tip has been forced through the first cross-slit valve and said first Luer slip tip extends through the entire first passage.

The Luer slip syringe tip is a conical fitting with a 6% taper, to which many female fittings, e.g. fittings to which a needle is attached, can be connected. The male and female fitting are held to each other by friction, that is, by interference fit. The Luer slip syringe tip is a standard fitting for medical instruments, and is described in ISO 80369-7:2010.

Preferably the first passage is further adapted to receive said first Luer slip syringe tip in that the valve body surface delimiting the first passage has a conical surface with a taper smaller than the Luer taper and with a diameter smaller than, but similar to, the first diameter of the first Luer slip syringe tip, so as to radially seal around said first Luer slip syringe tip. In this embodiment the Luer slip tip is inserted into the first passage until it gets stuck, whereby said first passage has been configured such that said Luer slip tip will only get stuck after it has been inserted so far that a top section of said tip has been forced through the cross-slit valve and extends through the entire passage.

Thus, the sealing between syringe tip and cap is a radial sealing on the conical surface of the of the valve body rather than at the cross-slit valve. Said radial sealing at the conical surface is expected to provide a more reliable sealing than a sealing at the cross-slit valve.

In another preferred embodiment the first tapered syringe tip is a first catheter syringe tip and the first passage being further adapted to receive said first catheter syringe tip in that a top section of said first catheter syringe tip can be forced through the first cross-slit valve and in that the passage seals around said first catheter tip when said top section of said first catheter tip has been forced through the first cross-slit valve and said first catheter tip extends through the entire first passage.

The catheter tip is a tapered syringe tip that is frequently used on syringes with relatively large volume. For instance, a Luer slip tip may be provided on a syringe with a volume of a few to a few tens of mL, while a catheter tip may be provided on a syringe with volume of several tens of mL. Moreover, catheter tips are commonly provided on a syringe with which a fluid is provided to a catheter or a gastrostomy tube.

In yet another preferred embodiment the first passage further comprises a first radial protrusion into the first passage. Said first protrusion is provided in the lower end of said first passage and creates a first constriction in the first passage. In this embodiment the first tapered syringe tip is a first catheter syringe tip and said first passage is further adapted to receive said first catheter syringe tip in that said first protrusion limits the insertion of said catheter syringe tip into the passage, in that when the top of said first catheter tip is provided on said first protrusion the first cross-slit valve can be opened by the underpressure created through retraction of the plunger of a first syringe onto which the first catheter syringe tip is provided and in that the first passage seals around said first catheter tip when said first catheter tip has been provided on said first protrusion.

The first cross-slit valve may be provided within said first constriction of the first passage. However, the first cross-slit valve may be provided below said first constriction.

Thus, in some embodiments of the invention the first syringe be forced through the first cross-slit valve so as to extend through the entire first passage, wherein in other embodiments the first syringe will extend into, but not through, the first passage.

The first cross-slit valve and second cross-slit valve both comprises a plurality of valve sections, preferably four valve section. The cross-slit valve preferably rapidly opens and closes in the presence of an underpressure, so as to remove through said repeated opening the underpressure.

In the embodiment where the first syringe is forced through the first cross-slit valve the valve sections in response to the pressure exerted on the top surface thereof bend downward and radially outward, so as to provide space for said tapered syringe tip. When said tapered syringe tip has been forced through said cross-slit valve in this way, the cross-slit valve sections may partially extend below the bottom surface of the valve body.

In the embodiment wherein the first syringe extends into the first passage until the protrusion provided therein, the first cross-slit valve the valve sections in response to the underpressure
created as described above bend upward and radially outward, so as provide an opening through which fluid can be withdrawn.

In an embodiment of the inventive cap wherein the first passage is adapted to receive a first catheter tip of which the insertion is limited by a first protrusion as described above, said first passage may be further adapted to receive a first Luer slip syringe tip having a first diameter in that said first Luer slip syringe tip is insertable into the first passage from the top surface of the valve body, in that said Luer slip tip is insertable into the first constriction in the first passage, in that the first protrusion seals around the first Luer slip syringe tip when said Luer slip tip has been inserted in the first constriction and in that a top section of said first Luer slip syringe tip can be forced through the first cross-slit valve so as to extend through the entire first passage.

The passage is thus adapted to receive both a catheter syringe tip, that can extend into, but not through, the first passage, and a Luer taper syringe tip, that can extend into and through the first passage. As the first protrusion limits the insertion of the catheter tip but not the Luer slip tip, the diameter of the Luer slip tip is smaller than the diameter of the catheter tip.

The second passage may be adapted to receive a second Luer taper syringe tip and/or second catheter syringe tip analogous to any of the embodiments described in the foregoing for the first passage.

The elastically deformable plastic valve body of the inventive cap allows for deformation under applied pressures. Such applied pressure may be the pressure exerted by a tapered syringe tip, as a result of which the cross-slit valve may for instance be forced open so that said tapered syringe tip extends through the entire passage and the passage seals around said tip. The deformable plastic valve body may for instance also deform under the pressure applied to it by a swivel nut, as will be described below, in order to seal between the container and the cap. Preferably, said elastically deformable plastic valve body is a unitary valve body or solid valve body. Moreover, preferably said plastic valve body is an elastomeric valve body.

The valve body comprises at least two passages and therefore two cross-slit valves, so as to allow a tapered syringe tip to be inserted into one of said cross-slit valves to withdraw fluid, whereas at the same time the one or more other cross-slit valves open in response to an underpressure in said container resulting from said withdrawal, so as to aerate said container. In fact, in a preferred embodiment of the invention the valve body has only two passages.

The valve body may nevertheless comprise more than two passages, e.g. three or four, when it is foreseen that more than two different tapered syringe tips will be used in the intended application.

Each of the cross-slit valves seals its passage when it is not forced open by the tapered syringe tip or opens in response to an underpressure. That is, the cross-slit valves are 'normally closed' cross-slit valves. The ability of the valve body to elastically deform aids in providing said normally closed state.

As both the forcing of a tapered syringe tip through said cross-slit valve and the occurrence of an underpressure take place when a syringe tip is inserted into any of the passages, each slit valve closes so as to seal its passage when no syringe tip is inserted into any one of the passages. As in this situation the passages are sealed, the container with the inventive needleless syringe connector cap can be turned upside down without any leakage through the cross-slit valves of the passages.

Preferably the bottom surface of the valve body comprises a receding surface portion, so as to form a recess in a lower portion of said valve body. The first passage and second passage end in said recess in the valve body. Such a recess may aid in extracting the last remainder of fluid from a nearly empty container. Moreover, the container may initially be provided with a removable sealing foil that seals the aperture at the top of the container. The cap is then provided to the container with the foil remaining in place until the first usage of the fluid. By providing said receding surface portion direct contact between cross-slit valves and foil is avoided, and therefore accidental crack formation or breakage of said foil by the cross-slit valves is avoided.

Each cross-slit valve comprises a top surface and a bottom surface. The valve sections of the cross-slit valves of the passages may lay in a plane when closed. However, preferably the cross-slit valves are dome-shaped, wherein in each cross-slit valve the bottom surface thereof is embodied as the convex surface of said dome-shaped cross-slit valve. Said dome shape aids in forcing said syringe tip through said cross-slit valve and aids in the sealing of said passages against the pressure exerted by fluid in the container, e.g. when said cap is provided on said container and said container and cap are tilted, possibly tilted upside down. In this way the dome-shaped cross-slit valve prevents unwanted outward opening.

The first cross-slit valve has a first top surface and a first bottom surface. In an embodiment, when said first cross-slit valve is closed the first bottom surface thereof is flush with an adjoining portion of the receding surface portion of the bottom surface of the valve body. Similarly, the second cross-slit valve has a second top surface and a second bottom surface, and in an embodiment when the second cross-slit valve is closed the second bottom surface thereof is flush with an adjoining portion of the receding surface portion of the bottom surface of the valve body. When in said embodiment the valve sections of the cross-slit valve open, they extend underneath said passage, and therefore their outward movement is not restricted by the surface delimiting the passage. As a result, forcing said syringe tip through said cross-slit valve so that it extends through the entire passage may be easier.

In a preferred embodiment the cap further comprises a swivel nut. Said swivel nut comprises a ring-shaped clamping portion and a hollow cylindrical securing portion. The corresponding valve body comprises a central fluid withdrawal portion and a sealing portion. The first and second passage extend through said fluid withdrawal portion and the sealing portion is provided radially outwards from said fluid withdrawal portion. The clamping portion of the swivel nut is provided on top of at least a portion of said sealing portion of the valve body.

In this embodiment a separate component, namely the swivel nut, is provided for securing said valve body to a container. This may in particular be beneficial when the valve body is provided above the aperture in the top of said container.

However, also other embodiments are possible, wherein the valve body is provided within the aperture, and wherein said valve body is adapted to secure itself to the container. For instance, said valve body may comprise an abutment on top of said valve body, said abutment upon assembly being provided on the top of the container surrounding the aperture thereof. When moreover the outer circumference of the portion of the valve body within the container is equal to the inner circumference of the container top, upon assembly said elastically deformable valve body may encounter sufficient friction with the container wall to maintain its position in the container, while at the same time the abutment prevents pressing said valve body further into said container.

The embodiment of the cap comprising a swivel nut is further beneficial, as it avoids leakage between the valve body and top of the container as the swivel nut presses the sealing portion onto the top of the container. Specifically, leakage from the aperture of the container, continuing underneath said sealing portion of the valve body in between the swivel nut and container to arrive at the exterior of the container is avoided.

Said swivel nut preferably comprises rigid plastic material, in order to clamp the elastically deformable valve body.

In a preferred embodiment the valve body further comprises a fixation portion radially outwards from an upper portion of said fluid withdrawal portion. Said fixation portion has a largest width larger than the inner circumference of the ring-shaped clamping portion of the swivel nut. It moreover has a groove extending radially into said valve body. The fixation portion is provided above said groove and said sealing portion is provided below said groove, so that in an assembled state an inner portion of the ring-shaped clamping portion is provided within said groove of the valve body and said fixation portion of the valve body is provided at least partially above said clamping portion of the swivel nut. In this way said valve body is fixed to said swivel nut, also when the cap has not yet been provided to a container.

Preferably the lateral dimension of the valve body are between 2 centimeter and 10 centimeter, preferably between 3 and 6 centimeter. The lateral dimensions of said valve body should be sufficient to provide at least two passages for Luer taper slip fitting tips and optionally also a radially extending sealing portion. The height of the valve body, in particular the fluid withdrawal portion thereof, is preferably between 5 mm and 15 mm. The sealing portion may have a thickness between 2 mm and 6 mm.

The present invention moreover relates to a system of a cap according to the present disclosure and a container having an aperture at its top, wherein said cap is provided at least partially in or above said aperture at the top of the container.

The container may for instance comprise rigid plastic, especially near the top of the container, but may for instance also comprise flexible plastic. The container may also comprise glass.

Preferably said container is provided with an externally threaded portion at a top portion of said container, and said cap is provided with swivel nut as described previously, said swivel nut comprising internal threads at a lower portion thereof. In this way said cap can be screwed onto said container so as to retain said cap onto said container.

In another embodiments the cap may be retained differently, for instance by providing to said elastically deformable valve body an outer portion that can be provided to, e.g. pulled over, the outer sides of the top portion of the container.

In the previous embodiments it is foreseen that the valve body of the cap is provided above the aperture at the top of the container. However, the valve body may also be provided in said aperture. In embodiments wherein the valve body is provided in said container the valve body may provide the means to secure itself to the container, e.g. through an interference fit as disclosed above in the description of the valve body.

The swivel nut that is preferably part of the cap of the inventive system may comprise, as described above, a ring-shaped clamping portion and a hollow cylindrical securing portion. The corresponding valve body comprises a central fluid withdrawal portion and a sealing portion. The first and second passage extends through said fluid withdrawal portion and the said sealing portion is provided radially outwards from said fluid withdrawal portion. The clamping portion of the swivel nut is provided on top of at least a portion of said sealing portion of the valve body. Therefore, when said cap is screwed onto said container the sealing portion is clamped in between a top surface of the container and the clamping portion of the swivel nut, so as to seal between the container and the cap.

The container may be filled, for instance partially filled, with various fluid products. For instance, said container may be filled with fluid animal food or fluid animal medication.

The container may be provided with a removable sealing foil that covers the aperture at the top of the container. This may for instance be done directly after the container is filled with a fluid when said filling takes place at a location remote from the location of assembly of cap and container. Moreover, the removable sealing foil may aid in maintaining the quality of the fluid over a certain period of time. Preferably, the cap and container allow to be assembled at the site of manufacturer without removing or damaging the removable sealing foil. In this assembled state said removable sealing foil is provided below the valve body. The end user then removes the removable sealing foil prior to the first withdrawal of fluid from said system of cap and container.

The present invention moreover relates to a system of a cap according to the present disclosure, a container having an aperture at its top, wherein said cap is provided at least partially in or above said aperture at the top of the container, and a first syringe with a first Luer taper slip fitting tip having a first diameter. The first passage of the valve body of the cap is adapted to receive said first Luer taper slip fitting syringe tips as has been disclosed above in connection with the inventive needleless syringe connector cap.

The present invention moreover relates to a method to withdraw fluid from a container. In said method use is made of a system of a cap, container and syringe according to the present disclosure. The method comprises the steps of:
  inserting the first syringe with first Luer taper slip fitting tip from the top surface of said cap into the first passage so that a top section of said tip is forced through the first cross-slit valve and extends through the entire first passage, wherein the first passage seals around said first tip when said top section of said tip has been forced through the first cross-slit valve and said tip extends through the entire first passage,
  withdrawing fluid from said container through said first tip into said first syringe, wherein the second cross-slit valve opens in response to an underpressure in said container resulting from said withdrawal, so as to aerate said container, and
  removing the syringe tip from the passage, after which the first cross-slit valve seals the first passage and the second cross-slit valve seals the second passage, so as to seal the container from the ambient.

Moreover, said container may be provided with a removable sealing foil that covers the aperture at the top of the container. The method in this situation prior to inserting the first syringe further comprises the steps of:
  removing said removable sealing foil from the container, thereby uncovering the aperture at the top of the container, and
  securing said cap at least partially in or above said aperture at the top of the container.

The invention will now be discussed with reference to the drawings. In the drawings.

With reference to the drawings embodiments and optional features of the cap will be described.

Figure 1:
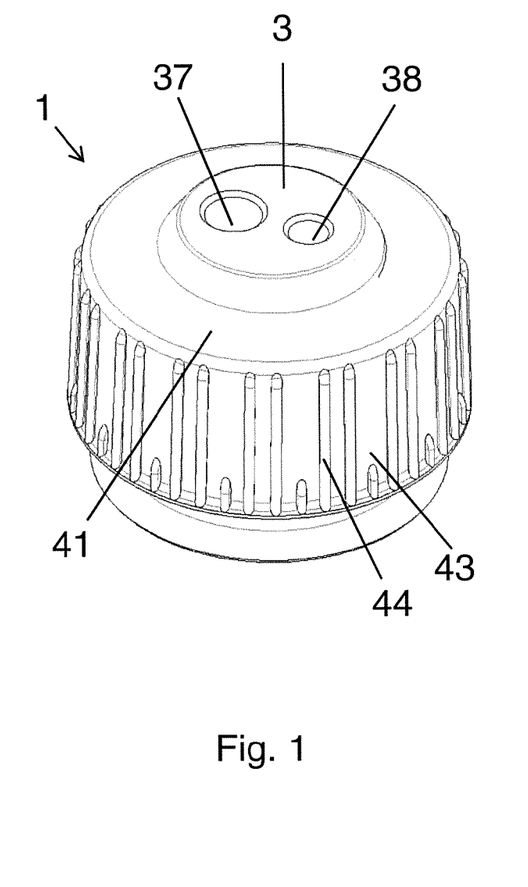
FIG. 1 shows a perspective view of a cap according to the invention.
Figure 2:
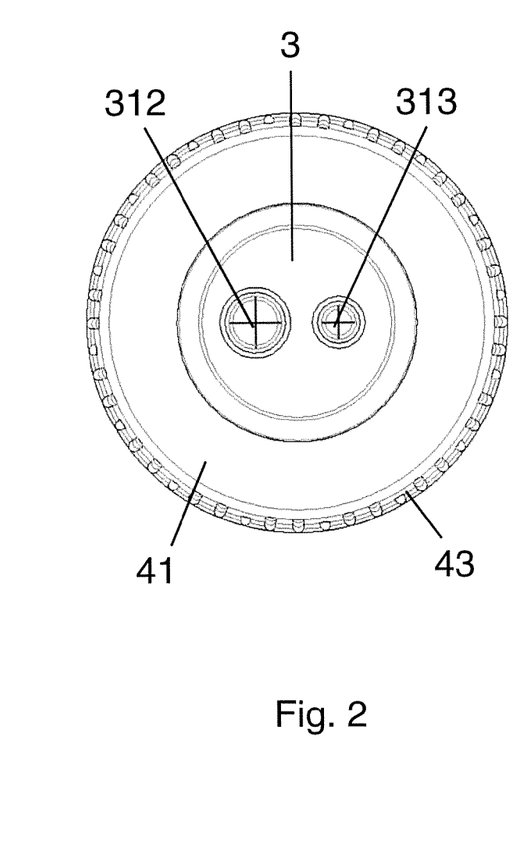
FIG. 2 shows a top view of the cap of FIG. 1.

An embodiment of the cap will now be described with reference to FIGS. 1-3. Note that in FIG. 3, as well as in the subsequent figures, the upright storage orientation of the cap and container is shown.

The cap 1 to be provided to a container 2 comprises in this embodiment a valve body 3 and a swivel nut 4.

As is preferred the valve body 3 is a monolithic molded body of elastically deformable material, e.g. of an elastomer.

As is preferred the swivel nut 4 is a monolithic molded body of plastic material.

The container 2, e.g. a blow molded plastic container, comprises a top portion 21 or neck comprising a lower cylindrical portion 22 with a first diameter and an upper cylindrical portion 23 with a second diameter. The outer surface of the lower cylindrical portion 22 is threaded with one or more threads 24. The second diameter here is slightly smaller than the first diameter, but may also be different, possible the diameters are the same.

The top of the top portion 21 of the container comprises a radially inward extending portion 25 surrounding an aperture 26.

The valve body 3 comprises a central fluid withdrawal portion 31, a fixation portion 32 and sealing portion 33. The fixation portion 32 and sealing portions 33 are both provided radially outwards from said central fluid withdrawal portion 31.

The fluid withdrawal portion 31 comprises a flat upper surface 34 with a first opening 35 and a second opening 36 of a first passage 37 and a second passage 38 respectively, which will be described in more detail below. The valve body 3 comprises a bottom surface 39.

The ring-shaped fixation portion 32 is provided radially outwards of a top portion of said fluid withdrawal portion, said fixation portion having in an upper portion a surface that is inclined downwards in the outward radial direction to facilitate the assembly of the valve body 3 and swivel nut 4. The upper portion of the valve body is thus frustoconically shaped. Below said inclined surface said fixation portion 32 comprises a groove 310 that extends radially into said valve body 3. The valve body 3 can be snapped into the opening of the swivel nut 4.

A ring-shaped sealing portion 33 is provided radially outwards of a bottom portion of said fluid withdrawal portion 31. The outer circumference of said sealing portion is similar in size to the width of the top portion of the container. In particular is said sealing portion provided with a protrusion 311 that extends downward from its lower outer edge, said protrusion forming an annular rib or ring on the lower outer edge of said sealing portion. Said rib has a circumference slightly larger than the diameter of the upper cylindrical portion of the container, allowing it to be provided on the outside of the upper cylindrical portion.

The swivel nut 4 comprises a ring-shaped planar clamping portion 41 around a central opening and a cylindrical securing portion 42. The inner circumference of said clamping portion is smaller than the largest width of said fixation portion 32 and similar to, but slightly larger than, the diameter of the groove 310 of the fixation portion.

The outer surface of the securing portion comprises one or more grip portions 43, e.g. comprising vertical ribs 44, to facilitate rotation of said swivel nut by a user. The inner surface of a lower portion of said securing portion is threaded with one or more threads 45.

To assemble the cap, the fixation portion 32 of the valve body 3 is pressed through the opening of the swivel nut 4 from the bottom side thereof so that the valve body is snapped onto the swivel nut 4. After assembly, as is shown in FIGS. 1-3, the clamping portion 41 of the swivel nut is provided on top of the sealing portion 33 of the valve body, with the innermost portion of said clamping portion provided in said groove 310 of the fixation portion. The upper portion of the fluid withdrawal portion 31 and the fixation portion 32 extend above said clamping portion 41. The fixation portion 32, together with the sealing portion 33, fixates said valve body 3 to said swivel nut 4.

Figure 3:
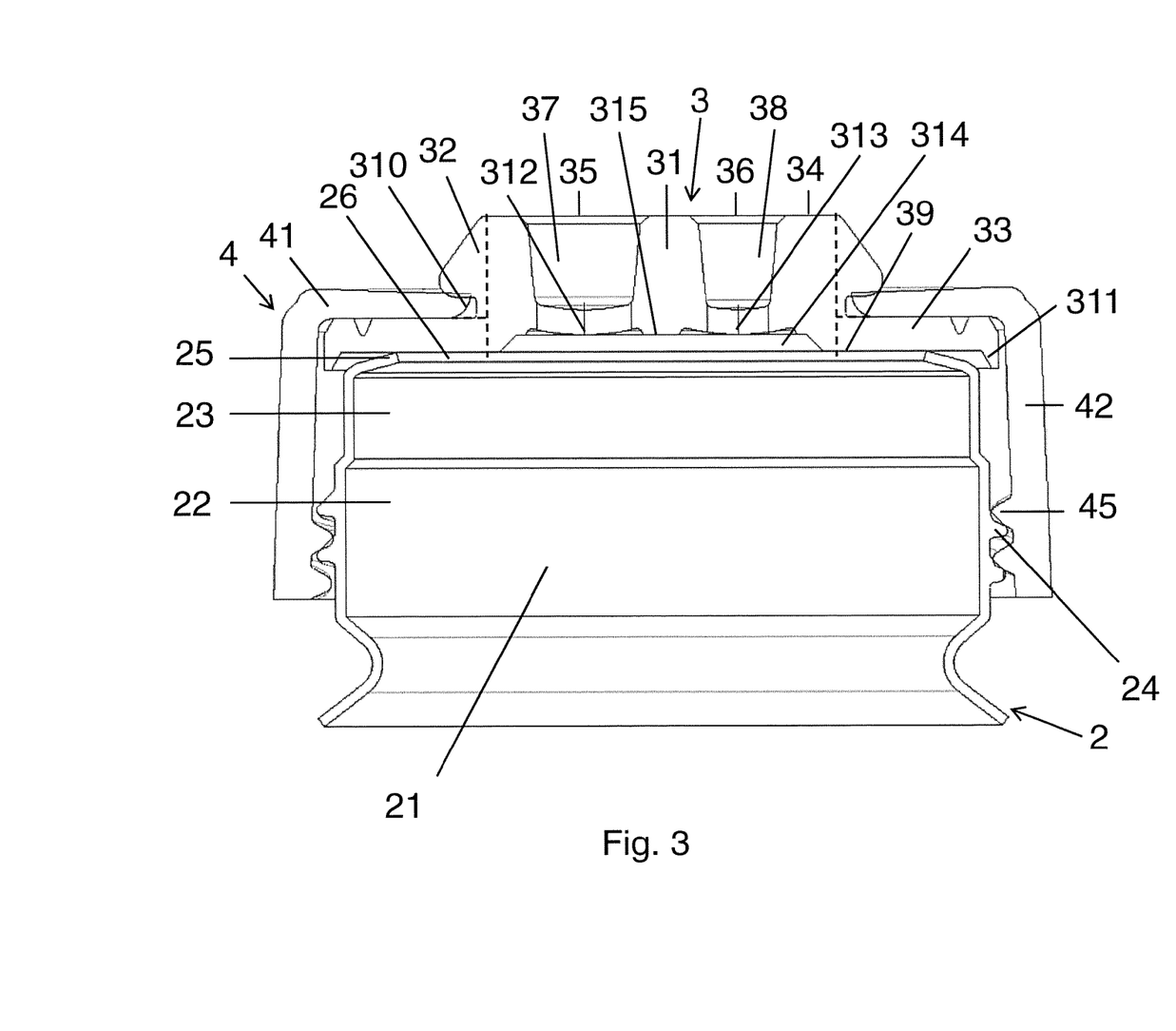
FIG. 3 shows a cross-sectional side view of the cap of FIG. 1 provided upon a container open at the top.

The swivel nut 4 and valve body 3 can then be screwed as a cap on said top portion of the container using the external threading 24 of the top portion of the container 2 and the internal threading 45 of the swivel nut 4, thereby obtaining the system of container and cap shown in FIG. 3.

By screwing said swivel nut 4 with the valve boy 3 onto said top portion of the container, the sealing portion 33 of the valve body 3 is clamped between the top end, here the inward extending portion 25 of the top portion 21, of the container and the clamping portion 41 of the swivel nut 4, thereby sealing the top portion 21 of the container so as to prevent leakage from the aperture 26 of the container underneath said sealing portion 23 of the valve body in between the swivel nut 4 and container 2 to the exterior of the container. The downward protrusions 311 at the lower outer edge of the sealing portion 33 provide additional sealing capacity to further prevent leakage.

In the shown embodiment the fluid withdrawal portion 31 comprises a first passage 37 and a second passage 38 extending from the top surface 34 to the bottom surface 39 of the valve body. The first passage 37 comprises at its lower end a first cross-slit valve 312, the second passage 38 at its lower end a second cross-slit valve 313, most clearly shown in FIG. 2.

The two slits of each cross-slit valve cross in the center of the valve, thereby forming four valve sections. The slit valves 312, 313 are embodied as aeration valves, that is, they open in response to an underpressure inside the container 2 with respect to the ambient pressure.

The first passage 37 is adapted to receive a first tapered syringe tip of a first syringe in that said first tip is insertable into said first passage 37 from the top surface 34 of the valve body and in that the first passage 37 seals around said first tip when said first tip has been inserted into the first passage 37. Similarly, the second passage 38 is adapted to receive a second tapered syringe tip of a second syringe in that said second tip is insertable into said second passage 38 from the top surface 34 of the valve body and in that the second passage 38 seals around said second tip when said tip has been inserted into the second passage 38.

In the present embodiment the first passage 37 is wider than the second passage 38, so that the first passage 37 is adapted to receive a tapered syringe tip with a larger diameter than the tapered syringe tip to which the second passage 38 is adapted.

When none of the cross-slit valves 312,313 are actually forced open, e.g. by introduction of a syringe tip into the respective passage, each cross-slit valve will effectively seal or close its passage, so as to seal the container from the ambient. The container 2 with cap 1, said container comprising a fluid, can in this situation be turned upside down without any leakage of said fluid through the valves 312, 313.

In the shown embodiment the lower surface 39 of the valve body comprises a receding surface portion 315 at the lower surface of the central fluid withdrawal portion, so as to form a recess 314 in the valve body relative to a surrounding region of the lower surface 39. The passages 37, 38 with cross-slit valves 312,313 end in the recessed area 314 of the lower surface 39 of the valve body 3.

In the shown embodiment the first cross-slit valve 312 and the second cross-slit valve 313 are both dome-shaped, as is apparent from FIG. 3, with the dome being directed towards the inside of the container.

The cross-slit valves 312, 313 are arranged at the lowermost end of the respective passage, so that here the convex surface of the dome-shape of each of the cross-slit valves 312, 313 forms part of the bottom surface 39 of the cross-slit valve. This arrangement of the cross-slit valves 312, 313 at the lowermost end of the respective passage, generally flush with the bottom surface 39, here the recessed area 314 thereof, for example facilitates the opening of the cross-slit valves 312,313, e.g. in view of the penetration of a conical plastic syringe tip through the valve which forces the valve open.

The passages 37, 38 above the cross-slit valve 312, 313 are conical, widening towards the top surface of the valve body, as preferred with a taper that corresponds to the taper of the syringe tip that is to be introduced into the passage. For example the taper is a 6% taper as is known in the field of syringes as a Luer taper. Preferably the tapering extends of the majority of the length of each passage, e.g. with the exception of a small entry bevel at the top surface.

As is preferred the slits in the valves 312, 313 extend over the entire diameter of the dome-shape, approximately corresponding to the narrowest width of the lower end of the respective passage 37, 38.

The withdrawal of fluid from a container provided with the inventive cap will be described with reference to FIGS. 4-6.

Figure 4:
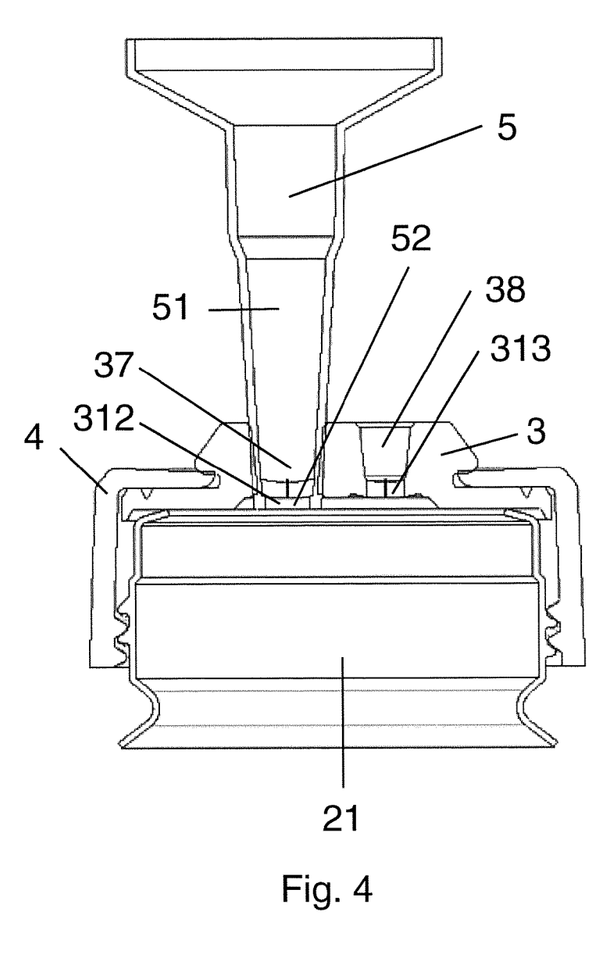
FIG. 4 shows the insertion of a syringe with a catheter tip into the cap of FIG. 1.

FIG. 4 shows an end portion of a first syringe 5 that is provided with a first tapered tip, here a first catheter tip 51. The first passage 37 of said valve body 3 is adapted to receive said first catheter syringe tip 51. The tip 51 is insertable into the first passage 37 of said valve body 3 from the top surface 34 thereof. The top section of said first tip 51 here is forced into the first cross-slit valve. The first passage 37 seals around said first catheter tip 51 when said top section 52 of said first catheter tip has been forced into the first cross-slit valve 312 and said first catheter tip 51 extends through the entire first passage 37.

The first catheter tip 51 exerts a mechanical pressure onto the top surface of the first cross-slit valve 312 at the bottom of said first passage 37, upon which the valve sections of said cross-slit valve 312 bend downward and outward, so that said top section 52 of said first catheter tip 51 is forced into and through said cross-slit valve 312, so that said tip 51 extends through the entire first passage 37.

With the syringe tip 51 extending through the entire first passage 37, the valve body seals around the first catheter tip 51 of the first syringe 5.

For withdrawal of fluid a user will hold the container 2 upside down with the syringe below the container. Fluid in the container 2 can now be drawn from said container by means of said syringe, and enter into the syringe 5 via the first catheter tip 51 thereof.

As fluid is drawn from said container 2 an underpressure or partial vacuum will arise in the non-collapsing container 2. This underpressure may hinder or render impossible a sufficient fluid withdrawal and is thus undesirable.

In the cap 1, when fluid is withdrawn from a container 2 using a syringe 5 with a first tapered syringe tip 51 introduced into the first passage 37, the second cross-slit valve 313, which is at the same time not being forced open by a syringe tip, opens in response to said underpressure so as act as an aeration valve and to provide ambient air to said container, thereby removing said underpressure. In other words, the second cross-slit valve 313 allows to aerate said container 2 when fluid is withdrawn via a syringe tip inserted into the other passage of the valve body. In practice the aeration will take place in minute opening events of the respective valve.

When sufficient fluid has been withdrawn from the container 2, possibly still with the container upside down, the user can retract the first tapered syringe tip, here catheter tip 51, from the first passage 37, and the first cross-slit valve 37 will then, due to its elasticity, automatically close and seal the first passage 37. As no further underpressure is created, the second cross-slit valve 313 will also automatically close and seal the second passage 38. As the first cross-slit valve 37 and second cross-slit valve 38 are closed, the cap 1 seals the container 2 from the ambient.

The first valve and second valve 312, 313 are embodied so that they will both act as a withdrawal valve as well as an aeration valve. Thus, as illustrated in FIGS. 5, 6, a second syringe 6 with a second tapered syringe tip, here a Luer slip syringe tip, 61 may be used to withdraw fluid from the container 2 via the other passage 38. The second passage 38 of the valve body 3 is adapted to receive said second Luer slip syringe tip 61 in that a top section 62 of said Luer slip syringe tip 61 can be forced into and possibly through the second cross-slit valve 313 and in that the second passage 38 seals around said second Luer slip tip 61 when said top section 62 of said second Luer slip tip 61 opens the second cross-slit valve 313 and said second Luer slip tip 61 extends through the entire second passage 38.

Said second tip 62 can be inserted into the second passage 38 from the top surface 34 of the valve body 3. The second tip 61 exerts mechanical pressure onto the top surface of the second cross-slit valve 313, upon which the valve sections of said cross-slit valve 313 bend downward and outward, so that said a top section 62 of the second tip 61 is forced into and possibly through said cross-slit valve 313, so that said tip 61 extends through the entire second passage 38.

In the present embodiment the second passage 38 is further adapted to receive said second Luer slip syringe tip 61 in that the valve body surface delimiting the second passage 38 has a conical surface with a taper the same or slightly smaller than the Luer taper and with a diameter the same or slightly smaller than, but similar to, the second diameter of the Luer slip syringe tip 61, so as to radially seal around said Luer slip syringe tip 61.

The second passage 38 seals, e.g. radially seals, around the second Luer taper slip fitting tip 61 of the first syringe 6. Fluid in the container 2 can now be drawn from said container to said second syringe 6 via the second Luer taper slip fitting tip 61 thereof. Upon withdrawal of fluid from said container through said second passage 38 the first cross-slit valve 312 allows to aerate the container.

Figure 5:
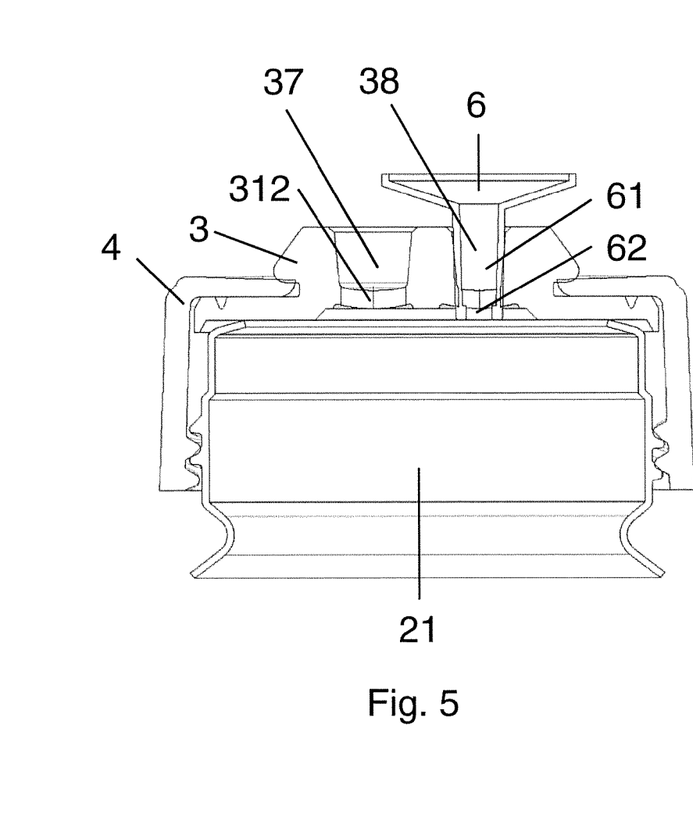
FIG. 5 shows the insertion of a syringe with a Luer slip tip into the cap of FIG. 1.
Figure 6:
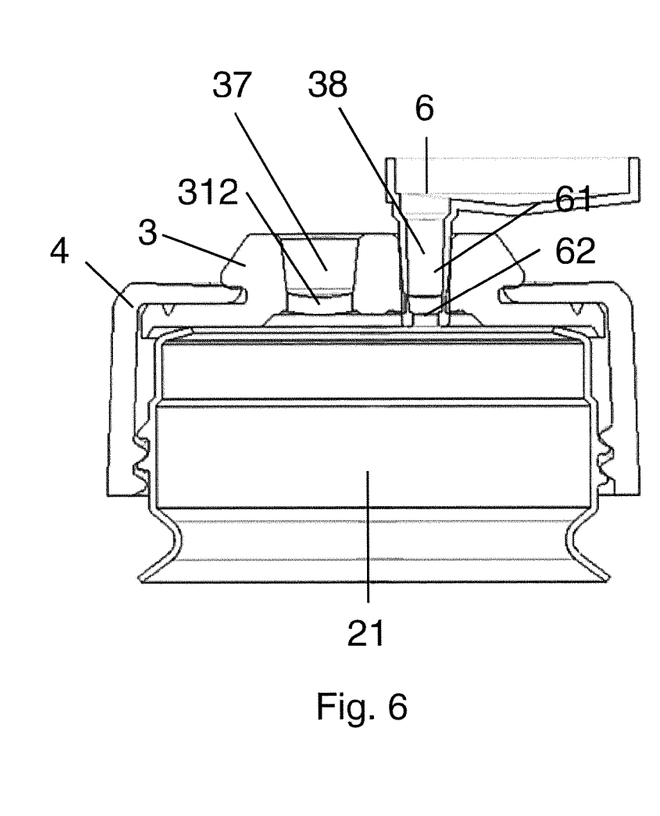
FIG. 6 shows the insertion of a syringe with an eccentric Luer slip tip into the cap of FIG. 1.

The Luer taper syringe tip may be placed centrally on the syringe, giving the central Luer slip syringe tip 61 shown in FIG. 5, but may also be placed off-center, giving the eccentric Luer slip syringe tip 61 of FIG. 6.

Figure 7:
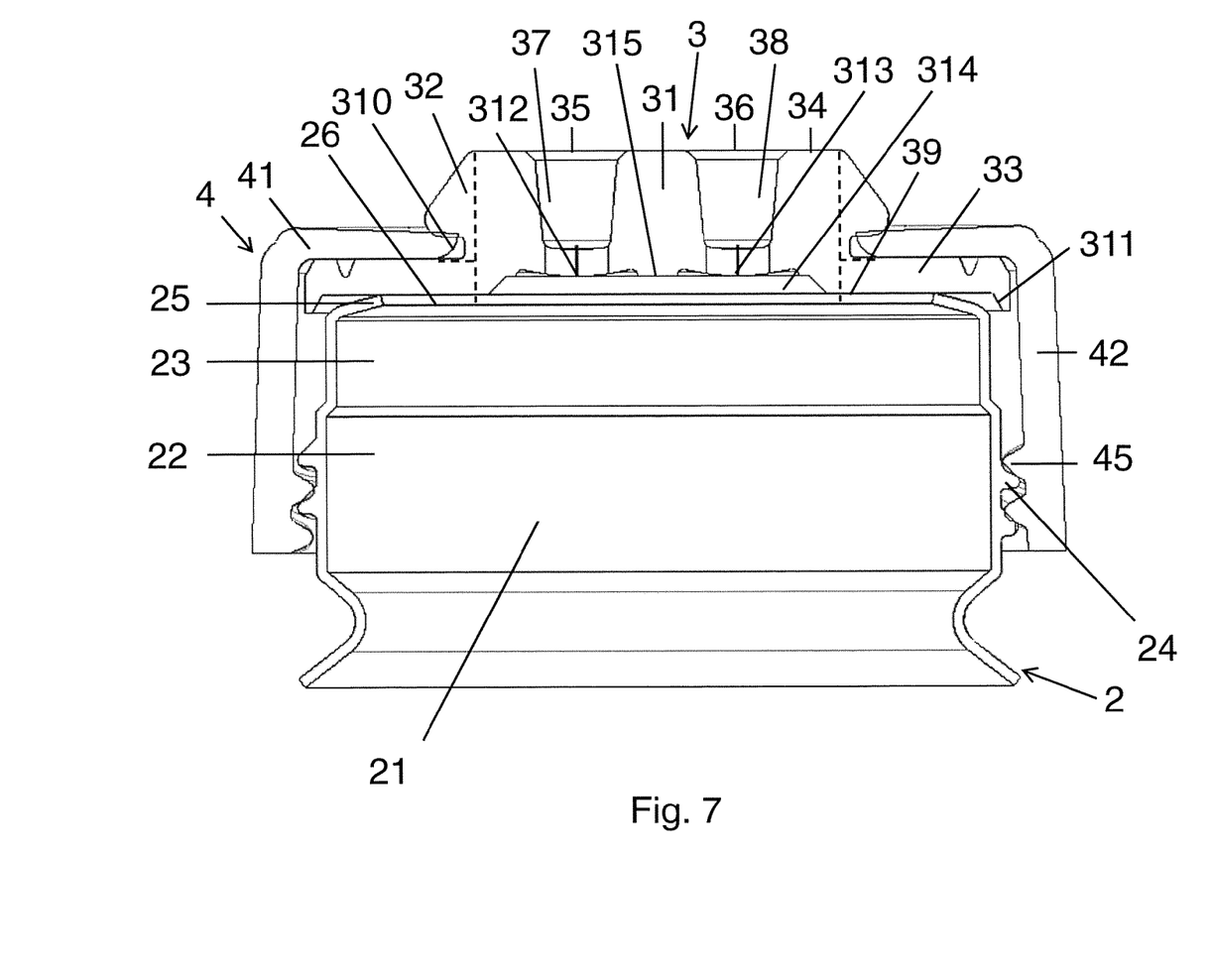
FIG. 7 shows another embodiment of a cap according to the invention.
Figure 8:
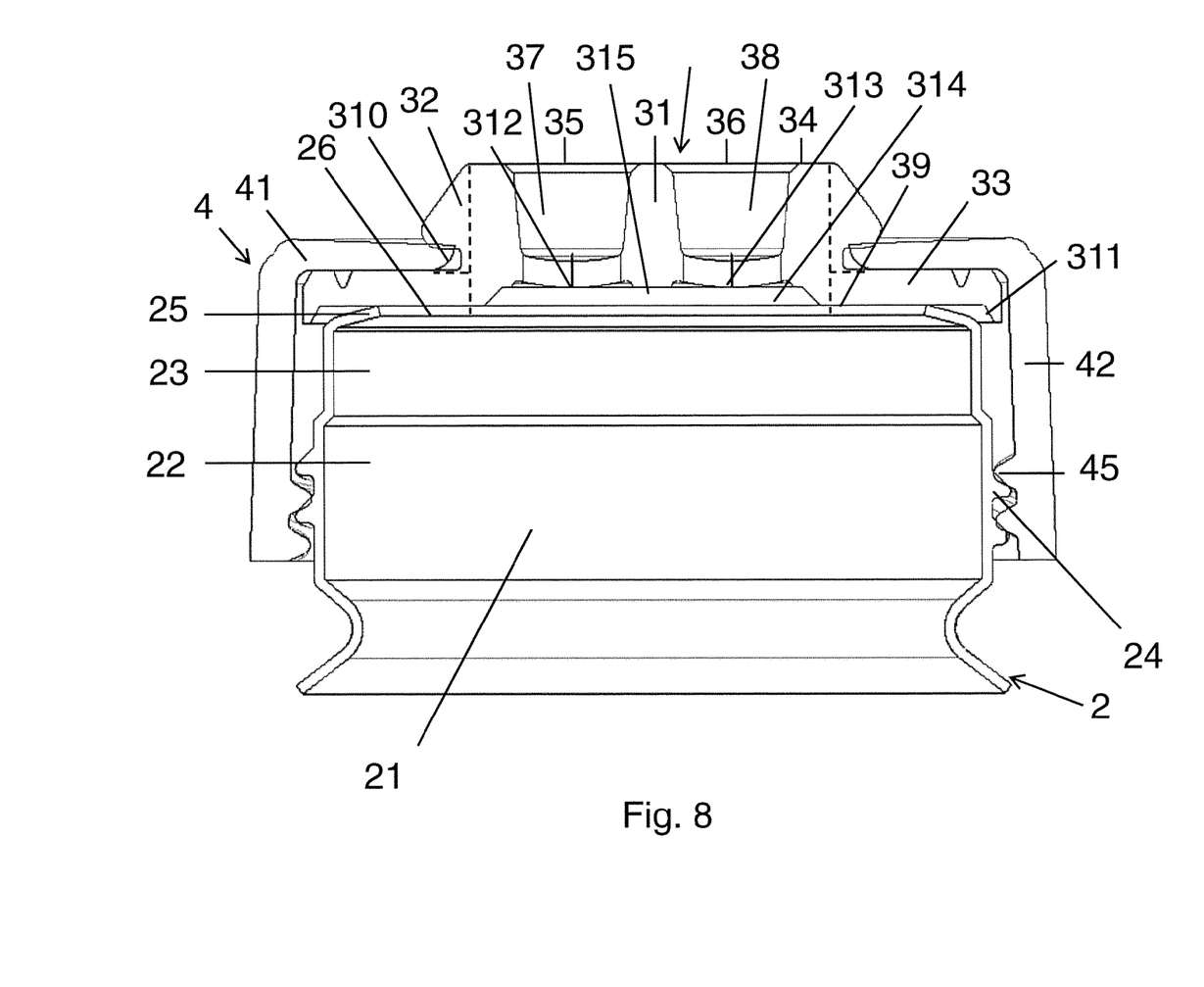
FIG. 8 shows yet another embodiment of a cap according to the invention.

The cap may also comprise two or more passages that adapted to the same type of tapered syringe tip, e.g. each of the two passages adapted to receive a Luer slip syringe tip with the same taper angle. These passages adapted to receive the same type of tapered syringe tip may also be adapted to receive the same type of syringe tip with the same diameter, e.g. two Luer slip syringe tips with the same taper and the same diameter. Such an embodiment with two identical passages 37,38 adapted to receive Luer taper slip syringe tips is shown in FIG. 7. Similarly, an embodiment with two identical passages 37,38 both adapted to receive catheter syringe tips, said catheter syringe tips having the same taper and diameter, is shown in FIG. 8.

Figure 9:
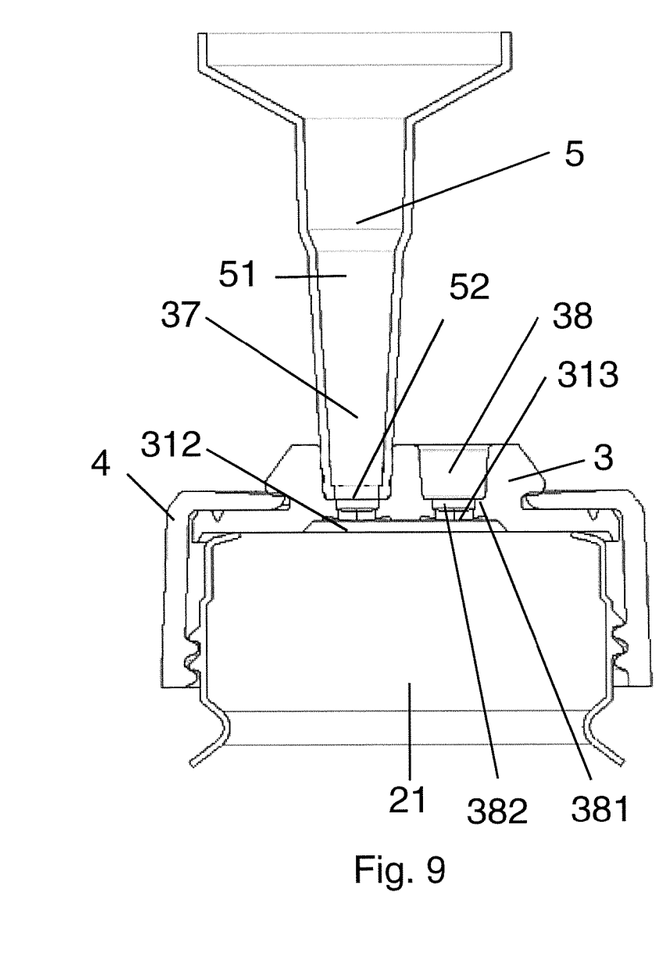
FIG. 9 shows yet another embodiment of a cap according to the invention, into which a catheter tip is inserted.
Figure 10:
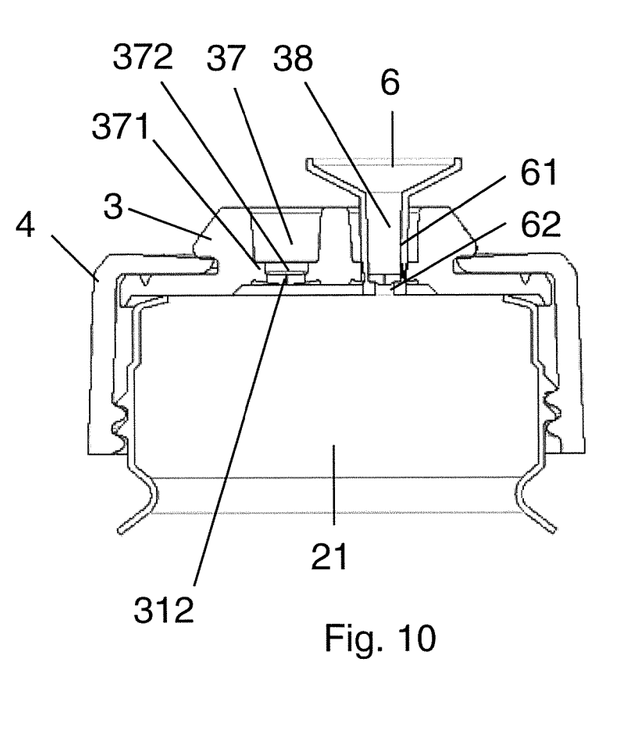
FIG. 10 shows the cap of FIG. 9, into which a Luer slip tip is inserted.

The embodiment of FIGS. 9 and 10 shows a cap with two identical passages 37,38, that are both adapted to receive both a catheter syringe tip 51 and a Luer slip tip 61. The passages 37,38 extend through the valve body and comprise cross-slit valves 312,313 embodied as aeration valves as described in the foregoing.

The first passage 37 comprises at the lowermost end thereof a radial protrusion 371 into the first passage 37, said first protrusion 371 provided in the lower end of said first passage 37 and creating a first constriction or shoulder 372 in the first passage. In the present embodiment the first cross-slit valve 312 is provided within said constriction 372. However, said first cross-slit valve 312 may also be provided below said constriction or shoulder 372.

The first passage 37 is adapted to receive a first catheter syringe tip 51 having a first diameter in that said first catheter tip 51 is insertable into the first passage 37 from the top surface 34 of the valve body 3 in that said first protrusion 371 limits the insertion of the catheter syringe tip 51 into the first passage 37, in that when the top 52 of said first catheter tip 52 is provided on said first protrusion 371 the first cross-slit valve 312 can be opened by the underpressure created through retraction of the plunger of a first syringe 5 onto which the first catheter syringe tip 51 is provided and that the first passage 37 seals around said first catheter tip 51 when said first catheter tip 51 has been provided on said first protrusion 371.

Moreover, the first passage 37 is further adapted to receive a first Luer slip syringe tip 61 having a first Luer slip tip diameter in that said first Luer slip syringe tip 61 is insertable into the first passage 37 from the top surface 34 of the valve body 3, in that said Luer slip tip is insertable into the first constriction 372 in the first passage 37, in that the first protrusion 371 seals around the first Luer slip syringe tip 37 when said Luer slip tip 61 has been inserted in the first constriction 372 and in that a top section 62 of said first Luer slip syringe tip can be forced through the first cross-slit valve 312 so as to extend through the entire first passage 37.

Thus, while the catheter tip 51 can only extend through a part of the passage, as it is limited by the first protrusion 371 as shown in FIG. 9, the Luer slip syringe tip 61 can be inserted into the same passage, into the constriction thereof and can extend through said entire passage, shown in FIG. 10 for a Luer slip syringe tip 61 inserted in to the second passage 38.

In the embodiment of FIGS. 9 and 10 the second passage 38 is adapted to receive both a catheter syringe tip 51 and a Luer slip syringe tip 61, in a manner analogous to the first passage 37. To this end said second passage 38 comprises a radial protrusion 381 into the second passage 38, said second protrusion 381 provided in the lower end of said second passage 38 and creating a second constriction 382 in the second passage 38.

Figure 11:
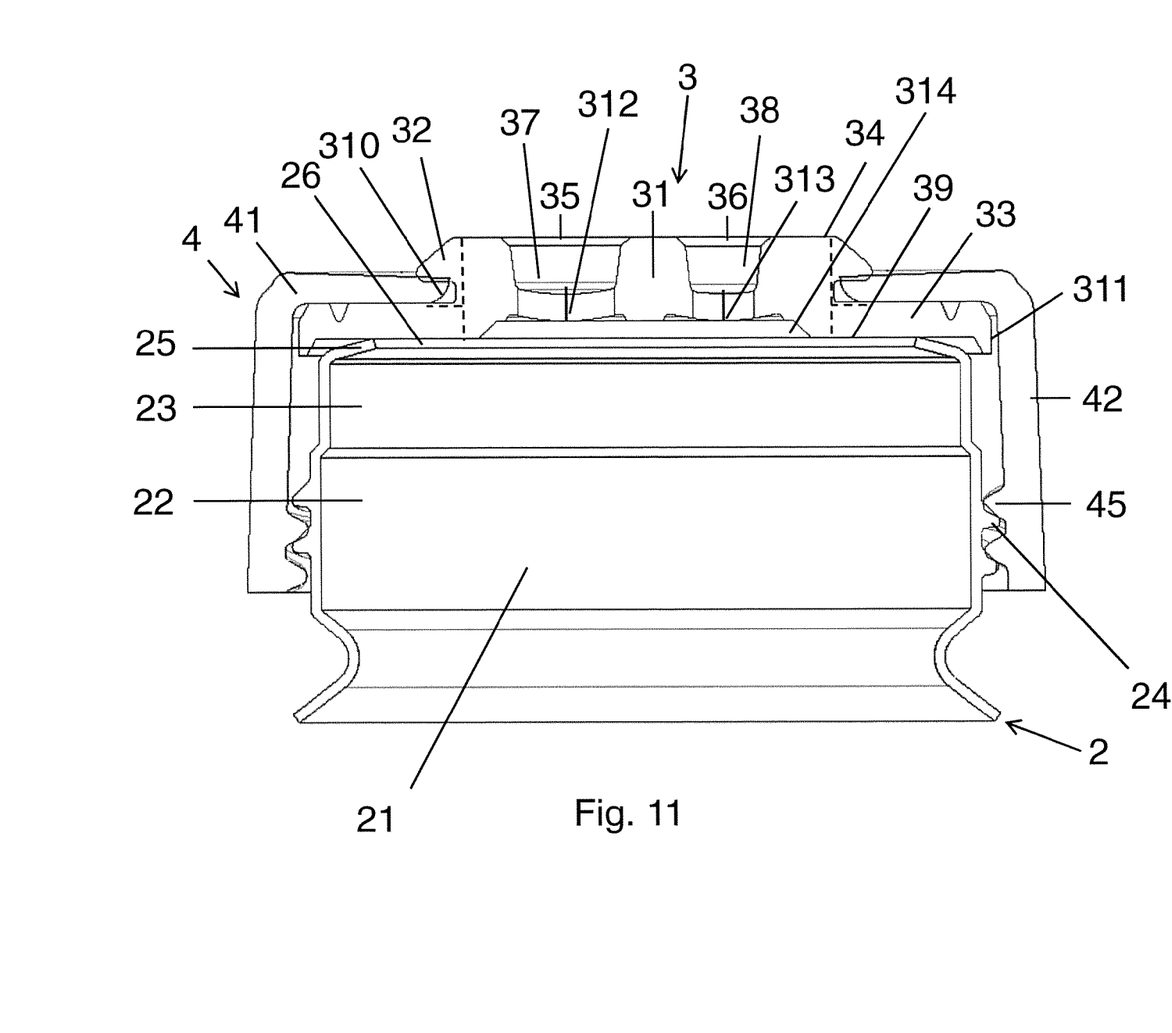
FIG. 11 shows a cap according to the invention with reduced height of the valve body.

The height of the fluid withdrawal portion 31 may vary in different embodiments of the inventive cap 1. The height of the fluid withdrawal portion 31 may for instance be reduced, as is shown in FIG. 11, so as to provide a more compact cap 1. Note that although the height of the fluid withdrawal portion 31 is reduced, the fixation portion 32 is still provided with a groove 310, through which said valve body 3 is fixed to the swivel nut 4.

The invention claimed is:

1. A needleless syringe connector cap to be provided to a container having an aperture at its top, said cap comprising:
    an elastically deformable plastic valve body to be provided in or above said aperture at the top of the container, said valve body having a top surface and a bottom surface,
    wherein said valve body comprises a first passage and a second passage, each passage extending through the valve body from the top surface to the bottom surface thereof, and
    wherein said first passage comprises a first cross-slit valve in the extreme lower end of said passage, wherein said first cross-slit valve is embodied as an aeration valve, and
    wherein said second passage comprises a second cross-slit valve in the extreme lower end of said passage, wherein said second cross-slit valve is embodied as an aeration valve, and
    wherein the first passage is adapted to receive a first tapered syringe tip having a first diameter, in that said first tip is insertable into the first passage from the top surface of the valve body and in that the first passage seals around said first tip when said tip has been inserted into the first passage, and
    wherein the second passage is adapted to receive a second tapered syringe tip having a second diameter, in that said second tip is insertable into the second passage from the top surface of the valve body and in that the second passage seals around said second tip when said tip has been inserted into the second passage, and
    wherein when fluid is withdrawn from a container to which the cap is provided through the first passage using a first tapered syringe tip to which said first passage is adapted, the second cross-slit valve opens in response to an underpressure in said container resulting from said withdrawal, so as to aerate said container, and
    wherein when fluid is withdrawn from a container to which the cap is provided through the second passage using a second tapered syringe tip to which said second passage is adapted, the first cross-slit valve opens in response to an underpressure in said container resulting from said withdrawal, so as to aerate said container.

2. The cap according to claim 1, wherein the first diameter is equal to, or larger than the second diameter.

3. The cap according to claim 1, wherein the first tapered syringe tip is a first Luer slip syringe tip, said first passage being further adapted to receive said first Luer slip tip in that a top section of said first Luer slip tip can be forced through the first cross-slit valve and in that the first passage seals around said first Luer slip tip when said top section of said first Luer slip tip has been forced through the first cross-slit valve and said first Luer slip tip extends through the entire first passage.

4. The cap according to claim 3, wherein the first passage is further adapted to receive said first Luer slip syringe tip in that the valve body surface delimiting the first passage has a conical surface with a taper smaller than the Luer taper and with a diameter smaller than, but similar to, the first diameter of the first Luer slip syringe tip, so as to radially seal around said first Luer slip syringe tip.

5. The cap according to claim 1, wherein the first tapered syringe tip is a first catheter syringe tip, said first passage being further adapted to receive said first catheter syringe tip in that a top section of said first catheter syringe tip can be forced through the first cross-slit valve and in that the passage seals around said first catheter tip when said top section of said first catheter tip has been forced through the first cross-slit valve and said first catheter tip extends through the entire first passage.

6. The cap according to claim 1, wherein the first passage further comprises a first radial protrusion into the first passage, said first protrusion provided in the lower end of said first passage and said first protrusion creating a first constriction in the first passage, wherein the first tapered syringe tip is a first catheter syringe tip, said first passage being further adapted to receive said first catheter syringe tip in that said first protrusion limits the insertion of said catheter syringe tip into the passage, in that when the top of said first catheter tip is provided on said first protrusion the first cross-slit valve can be opened by the underpressure created through retraction of the plunger of a first syringe onto which the first catheter syringe tip is provided and in that the first passage seals around said first catheter tip when said first catheter tip has been provided on said first protrusion.

7. The cap according to claim 6, wherein the first passage is further adapted to receive a first Luer slip syringe tip having a first diameter in that said first Luer slip syringe tip is insertable into the first passage from the top surface of the valve body, in that said Luer slip tip is insertable into the first constriction in the first passage, in that the first protrusion seals around the first Luer slip syringe tip when said Luer slip tip has been inserted in the first constriction and in that a top section of said first Luer slip syringe tip can be forced through the first cross-slit valve so as to extend through the entire first passage.

8. The cap according to claim 1, wherein the second tapered syringe tip is a second Luer slip syringe tip, said second passage being further adapted to receive said second Luer slip tip in that a top section of said second Luer slip tip can be forced through the second cross-slit valve and in that the second passage seals around said second Luer slip tip when said top section of said second Luer slip tip has been forced through the second cross-slit valve and said second Luer slip tip extends through the entire second passage.

9. The cap according to claim 8, wherein the second passage is further adapted to receive said second Luer slip syringe tip in that the valve body surface delimiting the second passage has a conical surface with a taper smaller than the Luer taper and with a diameter smaller than, but similar to, the second diameter of the Luer slip syringe tip, so as to radially seal around Luer slip syringe tip.

10. The cap according to claim 1, wherein the second tapered syringe tip is a second catheter syringe tip, said second passage being further adapted to receive said second catheter syringe tip in that a top section of said second catheter syringe tip can be forced through the second cross-slit valve and in that the passage seals around said second catheter tip when said top section of said second catheter tip has been forced through the second cross-slit valve and said second catheter tip extends through the entire second passage.

11. The cap according to claim 1, wherein the second passage further comprises a second radial protrusion into the second passage, said second protrusion provided in the lower end of said second passage and said second protrusion creating a second constriction in the second passage, wherein the second tapered syringe tip is a second catheter syringe tip, said second passage being further adapted to receive said second catheter syringe tip in that said second protrusion limits the insertion of said second catheter syringe tip into the passage, in that when the top of said second catheter tip is provided on said second protrusion the second cross-slit valve can be opened by the underpressure created through retraction of the plunger of a second syringe onto which the second catheter syringe tip is provided and in that the second passage seals around said second catheter tip when said second catheter tip has been provided on said second protrusion.

12. The cap according to claim 11, wherein the second passage is further adapted to receive a second Luer slip syringe tip having a second diameter in that said second Luer slip syringe tip is insertable into the second passage from the top surface of the valve body, in that said tip is insertable into the second constriction in the second passage, in that the second protrusion seals around the second Luer slip syringe tip when said second tip has been inserted in the second constriction and in that a top section of said second Luer slip syringe tip can be forced through the second cross-slit valve so as to extend through the entire second passage.

13. The cap according to claim 1, wherein the cap further comprises a swivel nut comprising a ring-shaped clamping portion and a hollow cylindrical securing portion, wherein the valve body comprises a central fluid withdrawal portion and a sealing portion, wherein the first and second passage extend through said fluid withdrawal portion, wherein said sealing portion is provided radially outwards from said fluid withdrawal portion, and wherein the clamping portion of the swivel nut is provided on top of at least a portion of said sealing portion of the valve body.

14. The cap according to claim 1, wherein the valve body further comprises a fixation portion radially outwards from an upper portion of said fluid withdrawal portion, said fixation portion having a largest width larger than the inner circumference of said ring-shaped clamping portion of the swivel nut, and a groove extending radially into said valve body, said fixation portion being provided above said groove and said sealing portion being provided below said groove, so that in an assembled state an inner portion of the ring-shaped clamping portion is provided within said groove of the valve body and said fixation portion of the valve body is provided at least partially above said clamping portion of the swivel nut, so as to fix said valve body to said swivel nut.

15. The cap according to claim 1, wherein the bottom surface of the valve body comprises a receding surface portion, so as to form a recess in a lower portion of said valve body, and wherein said first passage and second passage end in said recess in the valve body.

16. The cap according to claim 1, wherein each cross-slit valve has a top surface and a bottom surface, wherein each cross-slit valve is dome-shaped and wherein in each cross-slit valve the bottom surface thereof is embodied as the convex surface of said dome-shaped cross-slit valve.

17. The cap according to claim 1, wherein said first cross-slit valve has a first top surface and a first bottom surface, wherein when said first cross-slit valve is closed said first bottom surface is flush with an adjoining portion of the bottom surface of the valve body, and wherein said second cross-slit valve has a second top surface and a second bottom surface, wherein when said second cross-slit valve is closed said second bottom surface is flush with an adjoining portion of the bottom surface of the valve body.

18. A system comprising:

a container of the type where an underpressure is established in the container upon withdrawal of fluid from the container, said container having an aperture at its top, and a cap according to claim 1, wherein said cap is provided at the top of the container, wherein said container is provided with an externally threaded portion at a top portion of said container, and wherein said cap further comprises swivel nut with an internal thread, which retains said cap onto said container, wherein the swivel nut comprises a ring-shaped clamping portion and a hollow cylindrical securing portion, wherein the valve body comprises a central fluid withdrawal portion and a sealing portion, wherein the first and second passage extend through said fluid withdrawal portion, and wherein said sealing portion is provided radially outwards from said fluid withdrawal portion, wherein the clamping portion of the swivel nut is provided on top of at least a portion of said sealing portion of the valve body, and wherein when said cap is retained onto said container the sealing portion is clamped in between a top surface of the container and the clamping portion of the swivel nut, so as to seal between the container and the cap.

19. A system comprising:

a cap according to claim 1, a container having an aperture at its top, wherein said cap is provided at least partially in or above said aperture at the top of the container, and a first syringe having a first tapered tip with a first diameter, wherein the first passage of the cap is adapted to receive said first tapered syringe tip, and a second syringe having a second tapered tip with a second diameter, wherein the second passage of the cap is adapted to receive said second tapered syringe tip.

20. Method to withdraw fluid from a container, wherein use is made of a cap and/or a system according to claim 1, said method comprising the steps of:

inserting said first syringe with said first tapered syringe tip from the top surface of said cap into the first passage so that the first passage seals around said first tip when said top section of said tip has been inserted into the first passage, withdrawing fluid from said container through said first tapered tip into said first syringe, wherein the second cross-slit valve opens in response to an underpressure in said container resulting from said withdrawal, so as to aerate said container, and removing said first tapered tip from the first passage, after which the first cross-slit valve automatically seals the first passage and the second cross-slit valve seals the second passage, so as to seal the container from the ambient.

* * * * *